United States Patent [19]

Bredeweg

[11] Patent Number: 4,525,328
[45] Date of Patent: Jun. 25, 1985

[54] CARBON, HYDROGEN, AND NITROGEN ANALYZER

[75] Inventor: Roger L. Bredeweg, Stevensville, Mich.

[73] Assignee: Leco Corporation, St. Joseph, Mich.

[21] Appl. No.: 355,214

[22] Filed: Mar. 5, 1982

[51] Int. Cl.³ .................... G01N 1/22; G01N 31/10; G01N 31/12

[52] U.S. Cl. ..................... 422/80; 422/70; 422/89; 422/93; 436/115; 436/131; 436/133; 436/155; 436/157; 436/149; 436/159

[58] Field of Search ............ 422/78, 80, 89, 70, 422/93, 68, 83; 436/115, 157, 158, 159, 160, 155, 131, 133, 149

[56] References Cited

U.S. PATENT DOCUMENTS

| | | | |
|---|---|---|---|
| 3,296,435 | 1/1967 | Teal et al. | 422/78 |
| 3,698,869 | 10/1972 | Condon | 436/115 |
| 3,918,911 | 11/1975 | Reich | 422/71 |
| 4,271,124 | 6/1981 | Speeter | 422/78 |
| 4,401,763 | 8/1983 | Itoh | 422/80 |

FOREIGN PATENT DOCUMENTS 1279720 6/1972 United Kingdom .
1350300 4/1974 United Kingdom .

Primary Examiner—Michael S. Marcus
Attorney, Agent, or Firm—Price, Heneveld, Huizenga & Cooper

[57] ABSTRACT

The specification discloses an analyzer for determining the carbon, hydrogen, and nitrogen content of an organic material. The analyzer includes a vertically oriented, U-shaped furnace including a combustion chamber containing a crucible in which the sample is combusted into constituent gases and a reagent chamber containing a reagent through which the constituent gases must pass. A lance extends into the combustion chamber to guide the sample into the crucible and to direct oxygen onto the sample combusting in the crucible. The analyzer further includes an equilibration vessel and means for conveying the constituent gases to the vessel and past $CO_2$ and $H_2O$ infrared cells to monitor the products of combustion. Means are provided for conveying the equilibrated gases past the infrared cells to obtain readings relating to carbon and hydrogen content. A doser doses an aliquot of the equilibrated gas into a nitrogen measurement apparatus to obtain a reading relating to nitrogen content.

7 Claims, 4 Drawing Figures

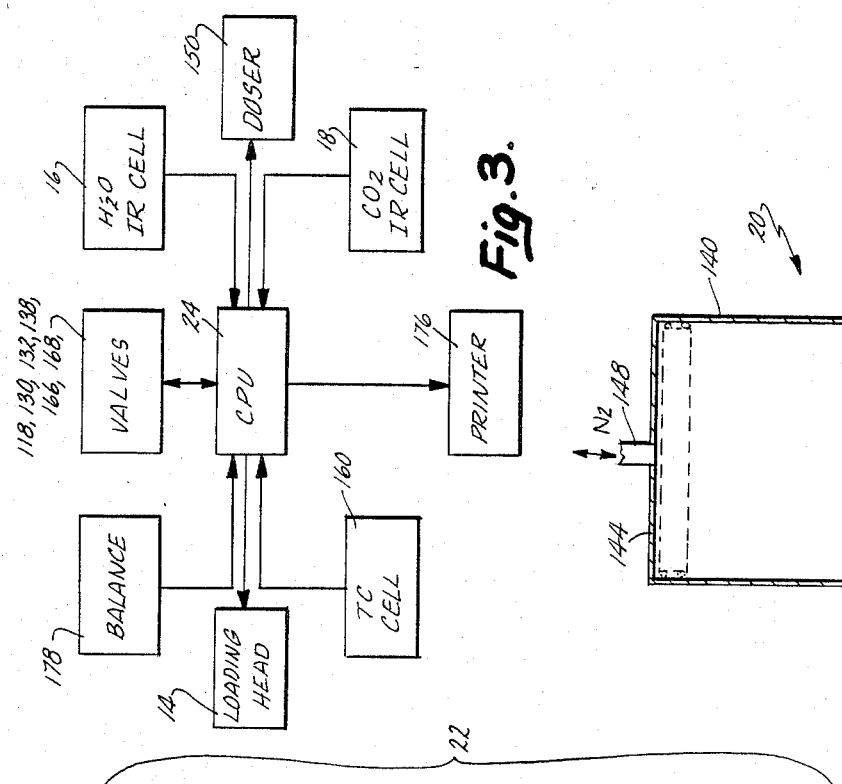
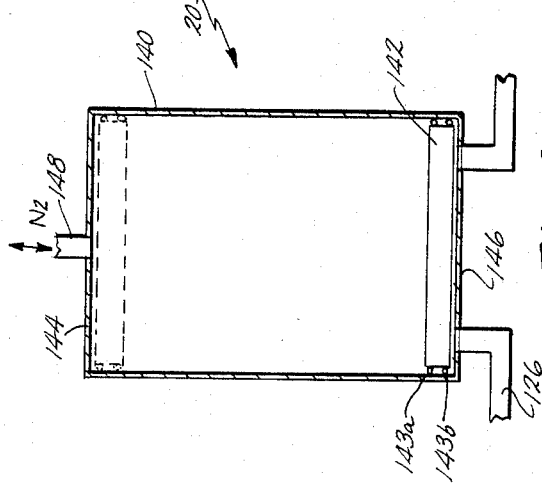
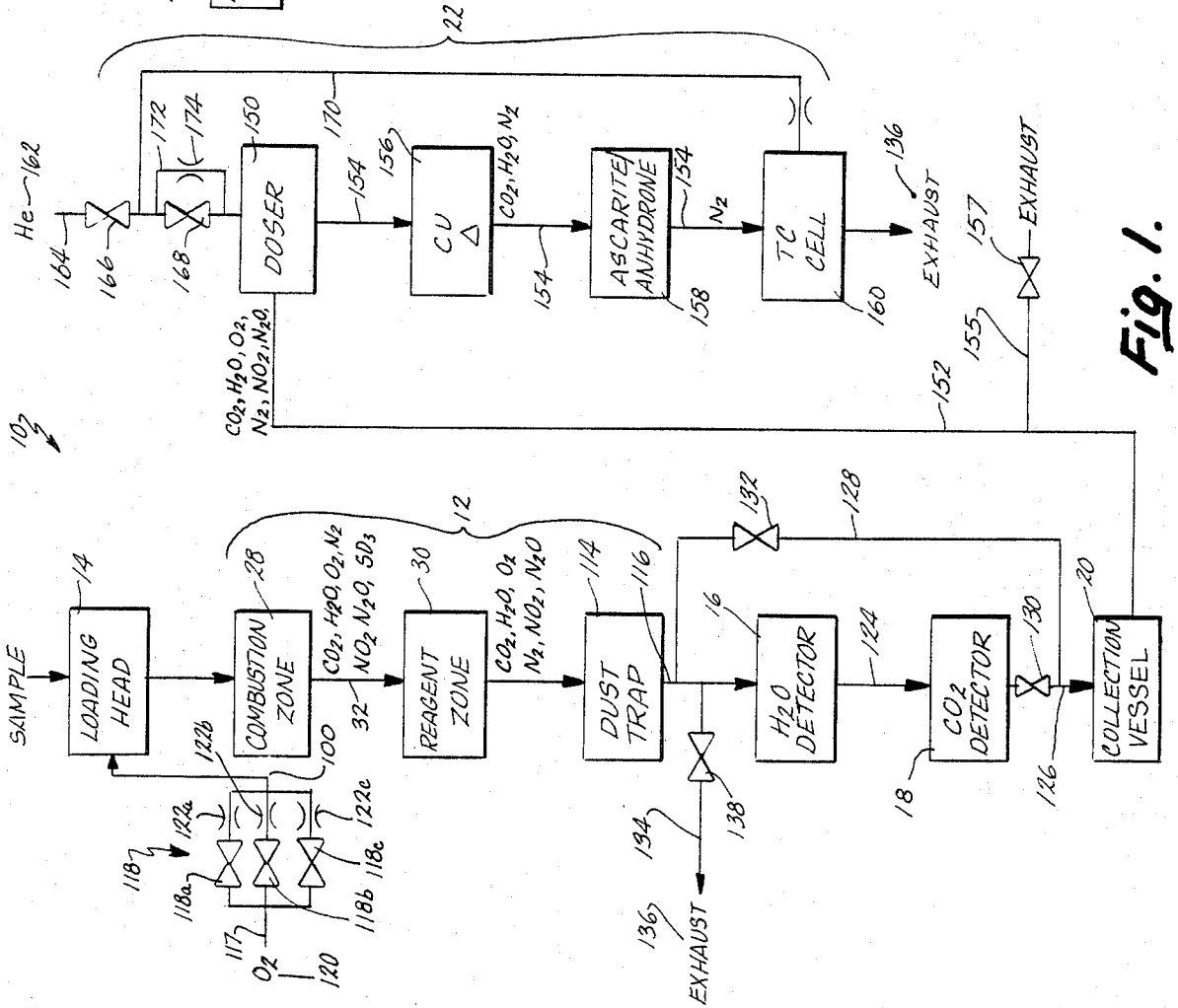

CARBON, HYDROGEN, AND NITROGEN ANALYZER

BACKGROUND OF THE INVENTION

The present invention relates to elemental analyzers, and more particularly elemental analyzers for combusting a sample into constituent gases for subsequent analysis.

The determination of the carbon, hydrogen, and nitrogen content of an organic material is necessary to a variety of determinations, such as the potential heat content of the material, as is particularly useful in evaluating coal and coke. Second, the elemental content is essential in the elemental analysis of the material as well as in determining the carbon-to-hydrogen ratio. Third, the elemental content provides an indication of the purity of an organic compound, for example graphite. Fourth, the nitrogen content of an organic is helpful in evaluating the material's potential for producing polluting nitrogen oxide.

The ASTM Standards for determining the carbon, hydrogen, and nitrogen content of an organic material are complicated and time consuming. The carbon and hydrogen are measured by burning a weighed quantity of the sample in a flow thru system and then fixing the products of combustion in an absorption train after oxidation and purification to measure the carbon dioxide and water produced. Nitrogen content is determined by converting the nitrogen to ammonium salts, decomposing the salts, distilling the resultant ammonia, and titrating the ammonia.

Although analyzers have been developed for analyzing the carbon, hydrogen, and nitrogen content of a material, these analyzers are not without their drawbacks. The analyzers typically combust the sample into constituent gases and then analyze the gases to calculate the elemental content. However, these machines usually require that the entire volume of gas produced during combustion be reduced to eliminate nitrogen oxides prior to the nitrogen measurement with a thermal conductivity cell. All carbon dioxide and water vapor must also be removed from the gas stream prior to the nitrogen measurement. Consequently, these analyzers must analyze only small samples to prevent the reducing agents and absorbers from becoming rapidly fouled. However, small samples lead to relatively large measurement errors. If the sample size is increased, the reducing agents and absorbers must be replaced relatively frequently.

Second, known machines typically provide a fixed combustion period to allow for complete sample destruction. However, when working with materials which combust relatively rapidly, the fixed combustion period is excessively long, resulting in excessively long analysis times. Although detection cells have been employed to monitor the combustion products to determine when combustion is essentially complete, the inclusion of these cells in an analyzer increases the cost and complexity of same.

Third, although some machines introduce oxygen into the furnace chamber during combustion to increase the rate at which the sample combusts, the oxygen is consumed relatively rapidly in the immediate area of combustion. Although a great deal of oxygen is generally available in the furnace, the oxygen concentration in the combustion area is relatively low.

Fourth, known analyzers typically provide a generally horizontally oriented combustion chamber communicating and aligned with a generally horizontally oriented reduction chamber. Therefore, gravity feed may not be utilized in dropping samples into the combustion chamber. Further, the aligned combustion chamber and reagent chamber require excessive horizontal space.

SUMMARY OF THE INVENTION

The aforementioned problems are solved by the present invention. Essentially, an analyzer is provided comprising a generally U-shaped analytical furnace having a vertically oriented combustion chamber in which a sample is combusted into constituent gases and a vertically oriented reagent chamber. A crucible is positioned within the combustion chamber, and a lance is provided for guiding samples into the crucible and for directing oxygen onto the sample during combustion. The analyzer further comprises an equilibration vessel and means for conveying the constituent gases into the vessel and past a first detection device responsive to the amount of one of the constituent gases. Additionally, means are provided for conveying the equilibrated gases from the vessel past the detection device after equilibration. Finally a doser is provided to dose an aliquot of the equilibrated gas into a second detection device responsive to a second of said constituent gases.

The generally vertically oriented U-shaped analytical furnace permits the samples to be gravity fed, or dropped, into the crucible within the combustion chamber. Additionally, the vertically oriented furnace is compact with the combustion chamber and reagent chamber generally parallel and adjacent to one another. The lance within the combustion chamber improves the gravity feed of samples because the lance guides the samples into the crucible. The lance improves sample combustion because oxygen is directed directly onto the sample during combustion.

Because the constituent gases are conveyed past the first detection device during sample combustion, the amount of the one gas can be monitored to monitor combustion and determine when combustion is essentially complete. Because the equilibrated gases are reconveyed past the first detection means after equilibration, the first detection means provides a signal indicative of the amount of the one gas in the equilibrated gases. Only this one detection means is required to both monitor combustion and to provide an elemental determination.

The fact that only a relatively small aliquot is removed from the equilibrated gases and introduced into the second detection device increases the useful life of any reduction and absorption devices in the second detection device because they need not reduce the entire volume of constituent gases. Additionally, a relatively large sample may be used to improve measurement and result accuracies.

These and other objects, advantages, and features of the invention will be more fully understood and appreciated by reference to the written specification and appended drawings.

BRIEF DESCRIPTION OF THE DRAWINGS

FIG. 1 is a schematic diagram of the analyzer of the present invention;

FIG. 3 is a schematic diagram of the computer control of the analyzer; and

FIG. 4 is a fragmentary, detailed, sectional view of the collection vessel.

DESCRIPTION OF THE PREFERRED EMBODIMENT

Figure 2:
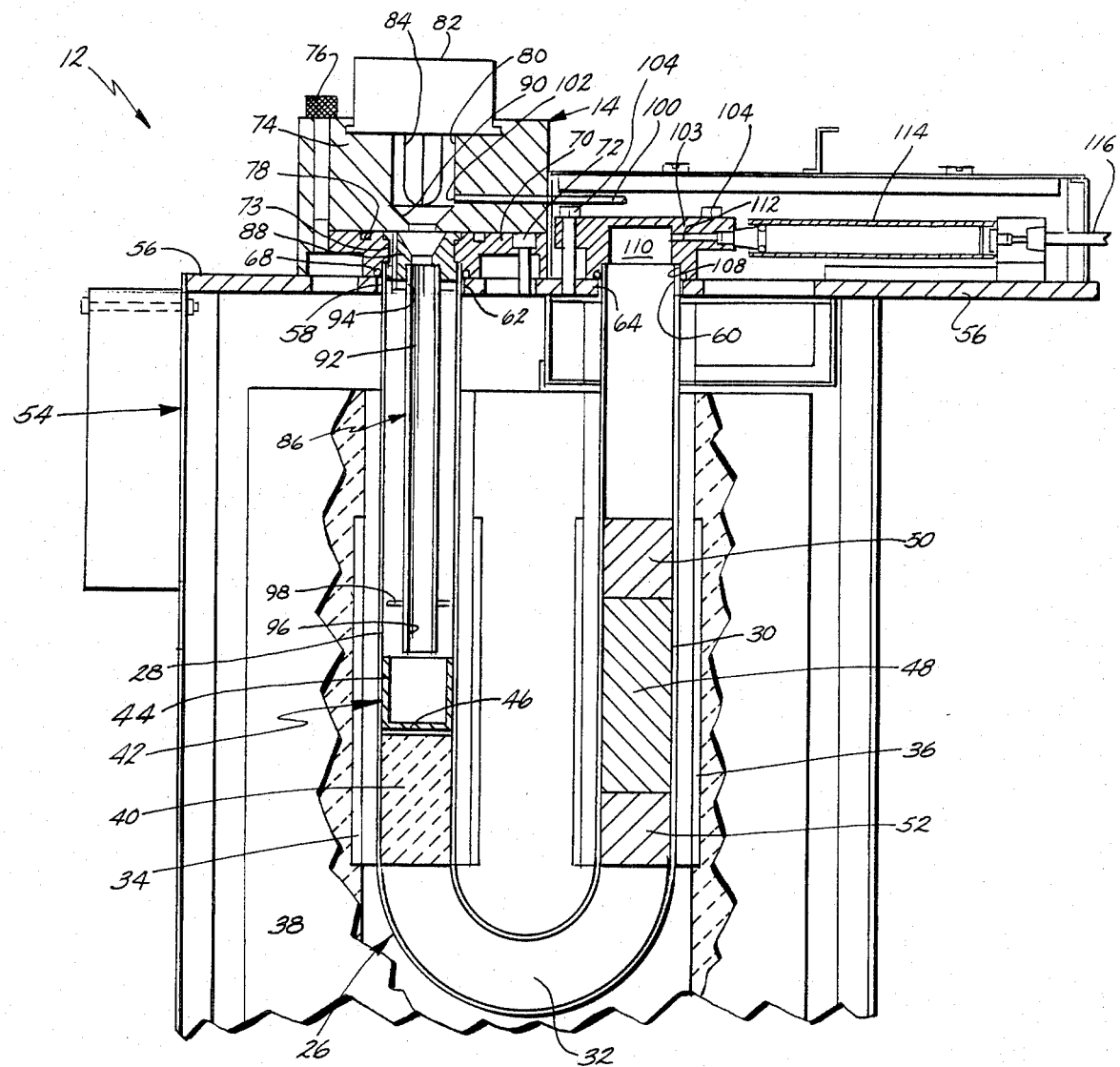
FIG. 2 is a detailed, fragmentary, sectional view of the furnace.

A carbon, hydrogen, and nitrogen analyzer in accordance with a preferred embodiment of the invention is illustrated in the drawings and generally designated 10. As seen in FIG. 1, analyzer 10 includes analytical furnace 12, loading head 14 for introducing samples into the analytical furnace, detectors 16 and 18 for analyzing two of the constituent gases produced during sample combustion, and collection vessel 20 for collecting and equilibrating the constituent gases resulting from combustion. Additionally, nitrogen analyzer 22 is connected to collection vessel 20 to draw an aliquot of the equilibrated gases to analyze the nitrogen content of the sample. Finally, computer 24 (FIG. 3) is included to provide overall analyzer control.

Turning more specifically to the construction of analytical furnace 12 (FIG. 2), it is seen that the furnace includes a vertically oriented, U-shaped combustion tube 26 having a generally vertically oriented combustion chamber or portion 28, a generally vertically oriented reagent chamber or portion 30, and a bight portion 32 communicating with and connecting the combustion and reagent portions. Combustion tube 26 is a generally tubular member having a circular cross section and a total volume of approximately 400 cubic centimeters. Resistance heater 34 is well known and surrounds combustion portion 28 and is capable of maintaining a temperature within the combustion portion of approximately 1,000° C. Similarly, resistance heater 36 is well known and surrounds reagent portion 30 and is capable of maintaining the temperature within reagent portion at approximately 1,000° C. Both of heaters 34 and 36 are powered in a manner well known to those having ordinary skill in resistance heating. Heaters 34 and 36 and tube 26 are supported within heater block 38. Furnace block 38 is supported within case 54, which includes a generally planar, horizontal top plate 56. Upper ends 58 and 60 of combustion portion 28 and reagent portion 30, respectively, extend through apertures 62 and 64, respectively, defined by plate 56.

Crucible support 40 is a generally cylindrical body secured within combustion portion 28 immediately above bight portion 32. Support 40 is generally porous so that gases may freely pass therethrough between combustion portion 28 and bight portion 32. Crucible 42 rests on support 40 and is a generally cup-shaped member having a cylindrical wall 44 integrally joined to planar bottom 46. Both of crucible 42 and crucible support 40 are fabricated of a material capable of withstanding the temperatures maintained within combustion portion 28.

Reagent 48 is positioned within reagent portion 30 and is held in position by quartz wool plugs 50 and 52 immediately above and below the reagent, respectively. Lower plug 52 is positioned immediately above bight portion 32. In the preferred embodiment, reagent 48 is calcium oxide which removes sulfur trioxide from any gases passing through the reagent. Alternatively, silver might be used as reagent 48 if chlorine were to be absorbed.

Loading head 14 is mounted on plate 56 and is sealed to upper end 58 of combustion portion 28 with O-ring 68. Loading head 14 is more fully disclosed in my U.S. Pat. No. 4,371,971, issued Feb. 1, 1983, entitled SAMPLE LOADING MECHANISM, assigned to the Assignee of the present invention, the disclosure of which is incorporated herein by reference. Loading head 14 includes lower block 70 secured to upper plate 56 by screw 72 and defining bore 73 sealed against upper end 58 with O-ring 68. Upper block 74 is secured to upper plate 56 by bolt 76 and sealed against lower block 70 with O-ring 78. Upper block 74 defines chamber 80 releasably sealed against ambient air by slide cover 82. Sample releasing jaws 84 are positioned within chamber 80 and are actuable to selectively retain or release a sample loaded therein. Samples may be introduced into jaws 84 when cover 82 is slid to an open position exposing the mechanism.

Lance 86 includes head block 88, secured in bore 73 and defining funnel bore 90, and generally tubular member 92 having an upper, open end 94, anchored in head block 88 and communicating with funnel bore 90, and a lower open end 96, proximate crucible 42. Member 92 is generally circular in cross section. Funnel bore 90 is generally axially aligned with both chamber 80 and tubular member 92 so that a sample released by jaws 84 will fall out of chamber 80 through funnel bore 90 and into lance member 86 to be guided into crucible 42. An annular ridge 98 extends outwardly from tubular member 92 to position lower end 96 generally concentrically within combustion portion 28. Upper end 94 of member 86 is positioned closely proximate head 14 to receive a sample from the loading head; and lower end 96 is positioned closely proximte crucible 42 to deposit a sample within the crucible.

Oxygen line 100 is connected to a source of pressurized oxygen at 40 p.s.i. in any well-known manner. Free end 102 of oxygen line 100 communicates with chamber 80 to provide a source of pressurized oxygen to the chamber. Because chamber 80 is sealed by cover 82, any oxygen entering the chamber must exit through lance 86 to be directed into crucible 42.

Head block 103 is secured to plate 56 by bolt 104 and is sealed to upper end 60 of reagent portion 30 by O-ring 106. Block 103 defines a bore 108 dimensioned to receive upper end 60, a generally cylindrical chamber 110 coaxially aligned with aperture 108, and bore 112 extending generally laterally from and communicating with chamber 110. Accordingly, gases exiting upwardly through reagent portion 30 must pass through chamber 110 and bore 112 which leads to dust trap 114 containing any dust filtering material well known to those skilled in the art. Dust trap 114 communicates with exit line 116.

Valve assembly 118 (FIG. 1) is interposed between oxygen source 120 and feed line 100. Assembly 118 includes three valves 118a, b, and c in parallel with one another and each in series with a restrictor 122a, b, and c, respectively. Each of restrictors 122 permits a different volume of oxygen to flow therethrough and in the preferred embodiment permits flows of 0.6 liters per minute, 1.5 liters per minute, and 5 liters per minute, respectively at 40 p.s.i. All of restrictors 122 feed into line 100 which, as described above, leads to chamber 80 in head 14 (see also FIG. 2).

$H_2O$ detector, or cell, 16 (FIG. 1) is any type of detector responsive to the amount of water vapor flowing therethrough and producing a signal indicative of said amount. Similarly, $CO_2$ detector, or cell, 18 is any type of carbon dioxide detector responsive to the amount of carbon dioxide flowing therethrough and producing a signal indicative of said amount. In the preferred embodiment detectors 16 and 18 are infrared cells. Line 116 leads from dust trap 114 in furnace 12 to $H_2O$ cell 16 (see also FIG. 2). Line 124 leads directly from $H_2O$ cell 16 to $CO_2$ cell 18. Finally, line 126 leads from $CO_2$ cell 18 to collection vessel 20. Shunt or bypass line 128 leads directly from line 116 to line 126, bypassing both of cells 16 and 18. Valve 130 is positioned in line 126 between cell 18 and line 128 to selectively permit or restrict gas flow through cells 16 and 18. Valve 132 is located in line 128 to selectively permit or restrict the flow of gas through that line. Line 134 leads from line 116 to exhaust 136 and contains valve 138.

Collection and equilibration vessel 20 (FIG. 4) includes cylinder 140 and piston 142 slidably mounted therein. O-rings 143a and b are positioned between piston 142 and cylinder 140 to seal the piston within the cylinder. Cylinder 140 includes a top wall 144 and a bottom wall 146. When piston 142 is in its uppermost position (as indicated in phantom in FIG. 4), the volume of vessel 20 is approximately 5,000 cc. Line 126 enters vessel 20 through bottom wall 146. Line 148 communicates with cylinder 140 through top wall 144 and is releasably connected to a source of pressurized gas, for example nitrogen, in any manner well known. Consequently, piston 142 may be forced downwardly by introducing pressurized gas into cylinder 140 through line 148 and may be shifted upwardly by releasing the pressure in line 148 and introducing gas through line 126.

Doser 150 (FIG. 1) is well known to those skilled in the art and is connected through line 152 to collection vessel 20 through bottom wall 146 (see also FIG. 4). Doser 150 is capable of drawing a 10 cc aliquot from vessel 20 through line 152 and depositing the aliquot in line 154. Consequently, the aliquot drawn by doser 150 comprises less than 2 percent, and more specifically 0.2 percent of the maximum volume of vessel 20. Line 155 vents line 152 to an exhaust 136 through valve 157. Line 154 from doser 150 leads sequentially to copper reduction chamber 156, ascarite/anhydrone chamber 158, thermal conductivity (TC) cell 160, and exhaust 136. Reduction chamber 156 is well known, containing elemental copper having a temperature of approximately 750° C. Chamber 158 is also well known, containing $CO_2$-absorbing ascarite and $H_2O$-absorbing anhydrone. TC cell 160 is also well known and is responsive to the amount of nitrogen flowing through the cell to produce a signal indicative of said amount. Helium source 162 is connected through line 164 to doser 150. Valves 166 and 168 are sequentially interposed in line 164. Line 170 leads directly from line 164, and more particularly from between valves 166 and 168, to TC cell 160. Shunt line 172 including restrictor 174 bypasses valve 168.

Central control for analyzer 10 is provided by computer 24 (FIG. 3), computer 24 is operably connected to loading head 14, $H_2O$ cell 16, $CO_2$ cell 18, doser 150, TC cell 160, printer 176, balance 178, and all of valves 118, 130, 132, 138, 157, 166, and 168. Computer 24 is programmed as is well known to those having ordinary skill in the programming art to issue control signals to valves 118, 130, 132, 138, 157, 166, and 168, doser 150, and loading head 14; to receive signals from detectors 16, 18 and 160, and balance 178; to compute the percent carbon, percent hydrogen, and percent nitrogen in the sample analyzed; and to print the results on printer 176.

OPERATION

Analyzer 10 (FIG. 1) is prepared for operation by connecting oxygen source 120 ahd helium source 162 to valve assembly 118 and 164, respectively. Heaters 34 and 36 (FIG. 2) are then actuated to produce temperatures of approximately 1,000° C. in both combustion portion 28 and reagent portion 30 of combustion tube 26. The copper within chamber 156 is heated to approximately 750° C.

An empty tin capsule (not shown) is then weighed on balance 178, which weight is read and recorded by computer 24 (FIG. 3). The sample (not shown) to be analyzed is then placed in the tin capsule. After being closed, the capsule is again weighed on balance 178, which weight is also read and recorded by computer 24. Next, the loaded capsule is placed in sample releasing jaws 84 (FIG. 2) by sliding cover 82 to its open position and placing the capsule between the jaws. Cover 82 is closed, sealing chamber 80 from the ambient air. Furnace 12, detectors 16 and 18, vessel 20, and lines 116, 124, 126, and 128 are purged by closing valve 138, opening valves 130, 132, and 157 and then introducing oxygen through selected ones of valves 118 (FIG. 1). Piston 142 is returned to its lowermost position (as shown in FIG. 4) by introducing nitrogen into cylinder 140. At this time, detectors 16 and 18 are zeroed due to the fact that only oxygen is present therein. Nitrogen analyzer 22 is purged by opening valves 166 and 168. Helium continually flows through line 170 and consequently TC cell 160 to provide a reference reading to the TC cell. Additionally, helium flows through shunt line 172 and consequently TC cell 160 to maintain the stability of cell 160.

After a sufficient purge period, computer 24 closes valves 138, 130, and 157 (FIG. 1) and opens jaws 84 (FIG. 2) to drop, or gravity feed, the sample into lance 86. The released sample first passes into funnel bore 90 where it is guided into tubular member 92. The sample then falls the entire length of tubular member 92 and is deposited in crucible 42. The capsule and sample are consumed in crucible 42 to produce constituent gases, including carbon dioxide, water, oxygen, nitrogen, nitrogen dioxide, nitrous oxide, and sulfur trioxide. All of these constituent gases, as well as the oxygen carrier, must flow through bight portion 32 because sample loading mechanism 14 seals the upper end 58 of combustion portion 28 from the ambient air. Consequently, the gases may escape combustion portion 28 only through bight portion 32.

As the sample is combusted, oxygen is introduced into chamber 80 in any of a variety of flows depending upon which of valves 118 are open. Additionally, the oxygen flows can be varied during combustion by opening and closing various patterns of valves 118. The flow pattern is operator selectable and is memorized and controlled by computer 24. Relatively low oxygen flow rates will be utilized with slow burning materials, such as coke, and relatively high flow rates will be used with rapidly combustible materials, such as coal. The oxygen introduced into chamber 80 must pass through lance 86 because the remainder of chamber 80 is sealed. Consequently, the oxygen is directed downwardly through lance 86 and is directed onto the combusting sample within crucible 42. This concentration and direction of oxygen onto the combusting sample greatly facilitates rapid and complete combustion. The constituent gases resulting from combustion pass through bight portion 32 and then through reagent portion 30. Reagent 48 extracts the sulfur trioxide, which absorbs water vapor, from the constituent gases, to insure the accurate determination of water vapor content. After flowing through reagent 48, the constituent gases then continue through chamber 110, bore 112, dust trap 114, and into line 116.

During combustion, valve 138 (FIG. 1) and doser 150 are both closed so that all of the constituent gases introduced into line 116 collect in vessel 20. During the initial combustion period, valve 130 is also closed, and valve 132 is open so that the constituent gases pass through line 128, bypassing detectors 16 and 18 to prevent the detectors from becoming contaminated due to heavy gas flow leaving deposits. After combustion is initiated, the nitrogen pressure in line 148 (FIG. 4) is released so that as the gases enter the vessel, piston 142 is forced upwardly until it eventually reaches its uppermost position as indicated in phantom. After an initial delay period from the start of combustion, valve 132 is closed and valve 130 is opened so that the constituent gases pass through detectors 16 and 18. Computer 24 then samples the reading at cells 16 and 18 which are responsive to the amount of water vapor and carbon dioxide, respectively, in the constituent gases to determine when combustion is essentially complete. That is to say that when the signals from detectors 16 and 18 fall below minimum values, computer 24 recognizes this as an indication that combustion is essentially complete and gaseous analysis can begin. Computer 24 then opens all of valves 118 until the pressure within collection vessel 20 reaches an absolute pressure of 975 millimeters. Then valves 130 and 132 are both closed and valve 138 opened to vent furnace 12 to the atmosphere. Additionally, valves 118b and c are closed, so that low oxygen flow is continued through furnace 12.

Computer 24 then initiates a delay period during which time the constituent gases within collection vessel 20 equilibrate or thoroughly mix to form an essentially homogenous mixture. After the equilibration delay period has expired, helium, upon entering doser 150, then draws an aliquot of equilibrated constituent gases from collection vessel 20 through line 152 and introduces same into line 154 with the helium. The mixture exiting the doser contains, among other compounds, carbon dioxide, water, oxygen, nitrogen, nitrogen dioxide, and nitrous oxide.

Valve 130 (FIG. 1) is then opened and nitrogen is introduced through line 148 (FIG. 4) into cylinder 140 forcing piston 142 downwardly. This causes the equilibrated gases to pass through line 126 (FIG. 1) to both of detectors 16 and 18 and out through line 134 to be vented to the atmosphere. After piston 142 has traveled a fixed distance, detectors 16 and 18 are sampled by computer 24 to provide an indication of the amount of water vapor and carbon dioxide respectively, in the equilibrated constituent gases. Valve 130 is then closed and valve 132 opened so that the exhausted gases will bypass the detectors to help keep the detectors relatively clean. Piston 142 continues its downward descent to its lowermost position as shown in FIG. 4 exhausting all of the gases therein to the atmosphere.

Meanwhile, the aliquot of gases carried on the helium stream within line 154 passes through copper reduction chamber 156. The copper reacts with the elemental oxygen and nitrogen/oxygen compounds to produce copper dioxide and elemental nitrogen. Consequently, the constituent gases exiting chamber 156 contain only carbon dioxide, water vapor, and elemental nitrogen on the helium carrier. These gases then enter ascarite/anhydrone chamber 158 wherein the carbon dioxide and water vapor are absorbed by the ascarite and the anhydrone, respectively, within the chamber. Consequently, only helium and elemental nitrogen exit chamber 158 to enter TC cell 160 through line 154. The TC cell then produces a signal responsive to the amount of nitrogen in line 154, which signal is read by computer 24.

Computer 24 (FIG. 3) then calculates the percent carbon, percent hydrogen, and percent nitrogen in the sample using the loaded capsule weight, the empty capsule weight, and the readings from detectors 16, 18, and 160. These results are then displayed on printer 176.

It should be understood that the above description is intended to be that of a preferred embodiment of the invention. Various changes and alterations might be made without departing from the spirit and broader aspects of the invention as set forth in the appended claims, which are to be interpreted in accordance with the principles of patent law, including the doctrine of equivalents.

The embodiments of the invention in which an exclusive property or privilege is claimed are defined as follows:

1. A system for analyzing the elemental content of a sample comprising:

furnace means for combusting a sample into constituent gases;

reservoir means for collecting and equilibrating the constituent gases;

first conduit and valve means actuable for conveying the constituent gases from said furnace means to said reservoir means during combustion of the sample;

second conduit and valve means actuable for conveying the constituent gases from said reservoir means for analysis, said first and second conduit means including a common conduit portion through which the constituent gases pass when conveyed to said reservoir means from said furnace means during combustion of the sample and when conveyed from the reservoir means during analysis;

a detector operably connected to said common conduit portion providing a signal responsive to the amount of at least one of the constituent gases within said common conduit portion; and control means operably connected to said first and second valve means and to said detector for controlling said first and second valve means and thereby controlling gas flow through said common conduit portion, said control means including means for opening said first conduit and valve means during combustion of the sample in said furnace means permitting the constituent gases to flow through said common conduit portion to said reservoir means until said signal falls below a minimum value indicating that sample combustion is essentially complete, said control means further including means for opening said second conduit and valve means after the gases are equilibrated within said reservoir means permitting the equilibrated constituent gases to flow through said common conduit portion whereupon said signal is indicative of the amount of the one constituent gas within the equilibrated constituent gases.

2. A system as defined in claim 1 further comprising means for selectively shunting the constituent gases around said detector to reduce contamination of said detector.

3. A system as defined in claim 1 wherein said detector comprises means for providing said signal responsive to the amount of carbon dioxide within said common conduit portion.

4. A system as defined in claim 1 wherein said detector comprises means for providing said signal responsive to the amount of water vapor within said common conduit portion.

5. A system as defined in claim 1 wherein said control means further comprises means for providing a delay period between closing of said first conduit and valve means and opening of said second conduit and valve means to improve equilibration of the gases within said reservoir means.

6. A system as defined in claim 1 further comprising a second detector operably connected to said common conduit portion providing a second signal responsive to the amount of at least a second of the constituent gases within said common conduit portion; and wherein said control means is further operably connected to said second detector; and wherein said control means opens said first conduit and valve means additionally until said second signal falls below a second minimum parameter; and wherein said second signal is indicative of the amount of the second constituent gas within the equilibrated constituent gases during opening of said second conduit and valve means.

7. A system as defined in claim 6 wherein said first detector comprises means for providing said first signal responsive to the amount of carbon dioxide within said common conduit portion; and wherein said second detector comprises means for providing said second signal responsive to the amount of water vapor within said common conduit portion.

* * * * *